United States Patent [19]
Barton

[11] 4,008,296
[45] Feb. 15, 1977

[54] ESTERS OF N-PHOSPHONOMETHYLGLYCINONITRILE

[75] Inventor: John Edward Duncan Barton, Wokingham, England

[73] Assignee: Imperial Chemical Industries Limited, London, England

[22] Filed: Aug. 15, 1975

[21] Appl. No.: 605,173

Related U.S. Application Data

[62] Division of Ser. No. 405,258, Oct. 11, 1973, Pat. No. 3,923,877.

[30] Foreign Application Priority Data

Nov. 8, 1972   United Kingdom ............. 51442/72

[52] U.S. Cl. .................................. 260/940; 71/86

[51] Int. Cl.$^2$ ...................... C07F 9/09; A01N 9/36
[58] Field of Search ................................... 260/940

[56] References Cited
UNITED STATES PATENTS 2,844,558   7/1958   Toy et al. ...................... 260/940 X

*Primary Examiner*—Anton H. Sutto
*Attorney, Agent, or Firm*—Cushman, Darby & Cushman

[57] ABSTRACT

Herbicidal compound, esters of N-phosphonomethylglycinonitrile, are disclosed. Also a process for preparing same.

2 Claims, No Drawings

ESTERS OF N-PHOSPHONOMETHYLGLYCINONITRILE

This is a division of application Ser. No. 405,258, filed Oct. 11, 1973, now U.S. Pat. No. 3,923,877.

This invention relates to chemical processes and more particularly to a process for making the herbicidal compound N-phosphonomethylgylcine.

According to the present invention, there is provided a process of preparing the compound N-phosphonomethylglycine, having the formula:

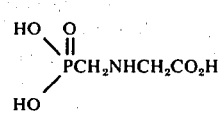

which comprises (a) reacting 1,3,5-tricyanomethylhexahydro-1,3,5-triazine with an ester of phosphorous acid having the formula:

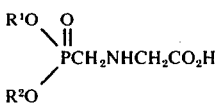

wherein $R^1$ and $R^2$ are hydrocarbyl or substituted hydrocarbyl radicals, in the presence of a catalyst comprising a hydrogen halide, a Lewis acid, a carboxylic acid halide, or a carboxylic acid anhydride to form an ester of N-phosphonomethylglycinonitrile, and (b) hydrolysing the ester of the N-phosphonomethylglycinonitrile, and recovering N-phosphonomethylglycine.

The process may be illustrated by the following reaction scheme:

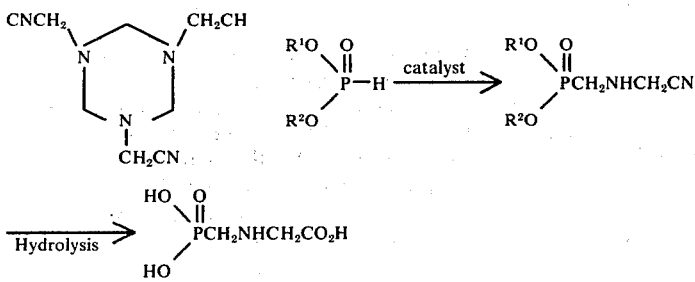

In the above scheme, the groups $R^1$ and $R^2$ are not involved in the reaction (a) between the ester of phosphorous acid and the 1,3,5-tricyanomethylhexahydro-1,3,5-triazine, and are removed when the ester of N-phosphonomethylglycinonitrile is subjected to hydrolysis (stage b). The nature of the groups $R^1$ and $R^2$ is therefore not critical, although of course groups which might interfere with the reactions involved in the process of the invention are to be avoided. Conveniently, the groups $R^1$ and $R^2$ are both aliphatic radicals, of 1 to 6, carbon atoms, optionally substituted by a phenyl group and may be, for example, alkenyl radicals, alkynyl radicals, alkyl radicals, or phenyl-containing radicals such as benzyl. Preferably the groups $R^1$ and $R^2$ are both alkyl radicals of 1 to 6 carbon atoms.

The catalyst used in the process of the invention is preferably hydrogen chloride or hydrogen bromide. Examples of catalysts comprising a Lewis acid, that is to say, an electron acceptor, include boron trifluoride, ferric chloride, and stannic chloride. Examples of catalysts which are acid halides derived from carboxylic acids include acetyl chloride and propionyl chloride. An example of a carboxylic acid anhydride catalyst is acetic anhydride. When an acid chloride or an acid anhydride is used as the catalyst, the product of the first stage (a) of the reaction may be the N-acyl derivative of an ester of N-phosphonomethylglycinonitrile. The N-acyl derivative is, however, hydrolysed to the free NH compound during stage (b) of the process of the invention. The ester of the phosphorous acid and the 1,3,5-tricyanomethyl-hexahydro-1,3,5-triazine may be used in stoichiometric proportions, that is to say, in the ratio of three molar proportions of the ester of the phosphorous acid to one molar proportion of the hexahydrotriazine. Conveniently however, the phosphorous acid ester may be used in excess to provide a solvent or diluent for the reaction.

Stage (a) of the process of the invention may be carried out with or without a diluent or solvent for the reaction. Suitable diluents, if used, include toluene, dioxan, dimethyl sulphoxide and dimethylformamide, and as mentioned above, an excess of the phosphorous acid ester used in the reaction. The temperature at which stage (a) of the process of the invention is carried out may vary depending for example upon the catalyst selected, or upon the boiling point of the diluent used, if any. In general however, a reaction temperature of from 15° to 100° Celsius is preferred, although higher or lower temperatures may be desirable in some circumstances. The product of stage (a) of the process of the invention may be isolated by conventional chemicals methods well known to those skilled in the art. By way of example, a typical procedure would be to dilute the reaction mixture with water at the end of the reaction period, make the mixture alkaline by addition of sodium hydroxidesolution, and extract the mixture with a water-immiscible solvent such as methylene chloride. The methylene chloride extracts could then be distilled to yield the product. The 1,3,5-tricyanomethyl-hexahydro-1,3,5-triazine used in the process of the invention is a known compound; its preparation is described, for example at page 355 of Collective Volume 1 of "Organic Syntheses,"Second Edition, published by John Wiley and Sons. In the latter publication it is referred to under the name of methyleneiminoacetonitrile. The esters of phosphorous acid used in the process of the invention are also a known class of compounds, of which examples, such as diethyl phosphite and dimethyl phosphite, are commercially available.

The second stage (b) of the process of the invention is preferably carried out by heating the ester of the N-phosphonomethylglycinonitrile with a concentrated aqueous solution of a mineral acid. Preferred mineral acids are hydrochloric acid, and hydrobromic acid, since these acids are volatile, which permits the N-phosphonomethylglycine to be isolated from the reaction mixture by concentrating the reaction solution and cooling it until the N-phosphonomethylglycine, which is of low solubility in aqueous solution, separates out.

The second stage (b) of the process of the invention may also be carried out by heating the ester of the N-phosphonomethylglycinonitrile with an aqueous, aqueous alcoholic, or alcoholic solution of an alkali, for example sodium or potassium hydroxide. In this case, a metal salt of N-phosphonomethylglycine will be obtained as the product. Further methods of carrying out the hydrolysis of esters of N-phosphonomethylglycinonitrile to N-phosphonomethylglycine will be apparent to those skilled in the art and the above methods are described only by way of example.

Esters of N-phosphonomethylglycinonitrile are new compounds. In another aspect, therefore, the invention provides esters of N-phosphonomethylglycinonitrile having the formula:

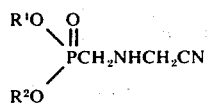

wherein $R^1$ and $R^2$ are each hydrocarbyl or substituted hydrocarbyl groups, useful as intermediates in the synthesis of N-phosphonomethylglycine.

N-Phosphonomethylglycine, as disclosed in Belgian Pat. No. 774,349, is a broad spectrum herbicide having little or no residual effect. Various methods have been proposed for its preparation. Example 14 of U.S. Pat. No. 3,160,632 for instance, describes the oxidation of glycinemethylene phosphinic acid with mercuric chloride to form N-phosphonomethylglycine. In view of the problems of environmental pollution associated with the use of mercury compounds, this method is obviously unsuitable for large scale manufacturing use. Belgian Pat. No. 774,349 describes the preparation of N-phosphonomethylglycine from glycine and chloromethylphosphonic acid. The chlorine atom in chloromethylphosphonic acid, however, is of low reactivity, and under the forcing conditions required to make the reaction take place, by products are formed, for example by hydrolysis of the chloromethylphosphonic acid. Another by product is the compound formed by reaction of two molar proportions of chloromethylphosphonic acid with one of glycine, that is to say, the compound of structure $HOCOCH_2N[CH_2PO_3H_2]_2$. Furthermore this method involves the prior preparation of chloromethylphosphonic acid. The process of the present invention has the advantage that the starting material, 1,3,5-tricyanomethylhexahydro-1,3,5-triazine, is readily available from cheap starting materials, namely sodium cyanide, ammonium chloride, and formaldehyde. The phosphorous esters also required as starting materials are also cheaply available.

The invention is illustrated by the following Example.

EXAMPLE

This Example illustrates the preparation of N-phosphonomethylglycine by a process according to the invention. 1,3,5-Tricyanomethylhexahydro-1,3,5-triazine (10.2 g.) dissolved in diethyl phosphite (40 ml; 41.1 g; 100% excess) was stirred and maintained at 40° C by cooling while the solution was saturated with hydrogen chloride gas. The passage of hydrogen chloride was then stopped and the mixture, from which a white solid precipitated, was stirred for 1 hour. Water was then added, and the mixture was made basic with sodium hydroxide solution. The mixture was extracted three times with methylene dichloride and the combined extracts dried over magnesium sulphate and evaporated in a vacuum. The residue was distilled and the fraction (1.8 grams) boiling at 148°–150° C. under a pressure of 0.2 millimetres of mercury was collected. Examination of the infra-red absorption spectrum showed a peak at 3330 $cm^{-1}$ assigned to the NH group and a peak at 2250 $cm^{-1}$ assigned to the CN group. Examination of the product by combined gas liquid chromatography and mass spectrometry showed that it comprised from 90 to 92% of the glycinonitrile derivative of the formula

together with from 8 to 10% of a derivative having the formula $NCCH_2N[CH_2P(OC_2H_5)_2]_2$. The nuclear magnetic resonance spectrum of a sample of the product in deuteriochloroform was consistent with this structure assignation.

The foregoing product (1.0 g.) was stirred and heated under reflux with 48% hydrobromic acid (6 ml.) for 3 hours. The pale yellow solution was cooled and evaporated in a vacuum. The pale yellow residue was dissolved in a small volume of boiling water (1 to 1.5 ml.). The solution so obtained was filtered and allowed to stand overnight. The white crystals of N-phosphonomethylglycine which separated (0.2 grams) turned yellow at 230° C and decomposed at 300° C. The infra red spectrum of this material was identical with that of an authentic sample of N-phosphonomethylglycine prepared from chloromethylphosphonic acid and glycine by the method described in Belgian Pat. No. 774,349. The nuclear magnetic resonance spectrum of a sample dissolved in deuterium oxide was also identical with that of an authentic sample of N-phosphonomethylglycine in deuterium oxide.

I claim:

1. An ester of N-phosphonomethylglycinonitrile, having the formula:

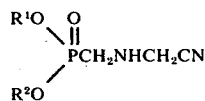

wherein $R^1$ and $R^2$ each represent an alkyl radical of from 1 to 6 carbon atoms.

2. An ester according to claim 1 wherein $R^1$ and $R^2$ are both ethyl.

* * * * *